(12) United States Patent
Gurupur et al.

(10) Patent No.: US 10,790,049 B2
(45) Date of Patent: Sep. 29, 2020

(54) METHOD AND SYSTEM FOR MANAGING HEALTH CARE PATIENT RECORD DATA

(71) Applicant: UNIVERSITY OF CENTRAL FLORIDA RESEARCH FOUNDATION, INC., Orlando, FL (US)

(72) Inventors: Varadraj Gurupur, Oviedo, FL (US); Ayan Nasir, Montverde, FL (US); Xinliang Liu, Oviedo, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 552 days.

(21) Appl. No.: 15/279,668

(22) Filed: Sep. 29, 2016

(65) Prior Publication Data

US 2017/0091394 A1    Mar. 30, 2017

Related U.S. Application Data

(60) Provisional application No. 62/234,792, filed on Sep. 30, 2015.

(51) Int. Cl.
*G16H 10/60* (2018.01)
*G06F 19/00* (2018.01)

(52) U.S. Cl.
CPC ............. *G16H 10/60* (2018.01); *G06F 19/00* (2013.01)

(58) Field of Classification Search
CPC ................................ G16H 10/60; G06F 19/00
See application file for complete search history.

(56) References Cited

U.S. PATENT DOCUMENTS

| 7,403,942 B1* | 7/2008 | Bayliss ................. G06F 16/215 707/748 |
| 8,412,542 B2* | 4/2013 | Mok ..................... G06F 19/325 705/3 |
| 8,538,989 B1* | 9/2013 | Datar .................... G06F 16/313 707/780 |
| 9,311,401 B2* | 4/2016 | Uy ..................... G06F 16/24578 |
| 2003/0220920 A1* | 11/2003 | Lake ........................ G06F 16/20 |
| 2005/0171941 A1* | 8/2005 | Chen ...................... G06Q 10/02 |
| 2006/0173924 A1* | 8/2006 | Wotton .................... G06F 16/20 |

(Continued)

FOREIGN PATENT DOCUMENTS

EP    0917078 A1 *  5/1999   ............. G16H 50/20

*Primary Examiner* — Aryan E Weisenfeld
*Assistant Examiner* — Steven G Sanghera
(74) *Attorney, Agent, or Firm* — Nicholas Pfeifer; Smith & Hopen, P. A.

(57) ABSTRACT

A method for managing health care patient record data including: associating, by a processor, native health care patient record data of a first patient stored in a database to a plurality of data fields, wherein the native health care patient record data of the first patient represents the first patient's health care record; assigning, by a processor, a relative importance weight score to each of the plurality of data fields; and generating, by a processor, a record strength score of the first patient's health care record based on the relative importance weight score assignments. The record strength score indicates a percentage of the first patient's health care record that contains important native health care patient record data.

20 Claims, 13 Drawing Sheets

(56) References Cited

U.S. PATENT DOCUMENTS

| | | | |
|---|---|---|---|
| 2013/0144790 A1* | 6/2013 | Clements | G16H 10/60 |
| | | | 705/51 |
| 2015/0106390 A1* | 4/2015 | Fuchs | G06F 16/23 |
| | | | 707/749 |
| 2015/0294069 A1* | 10/2015 | Shah | G06Q 30/018 |
| | | | 705/3 |

\* cited by examiner

▽ Template

Last Name,First Name,DoB,Address,Phone #,Email,Ins Co,Ins Group #,Ins Policy #,Med History,Allergies,Weight,Height,Age,Race ▽ PatientFiles P1,P1,2/22/54,Complete,8948217934,Complete,N/A,N/A,8495985914,Complete,N/A,292,77,57,Blue
P2,P2,7/17/64,Complete,9620186899,Complete,N/A,N/A,3354734600,9601255657,Complete,Complete,315,56,47,N/A
P3,P3,6/16/85,Complete,9832107225,N/A,N/A,4085607516,N/A,Complete,Complete,214,84,26,Red
P4,P4,N/A,N/A,2486894508,Complete,N/A,N/A,0838031608,Complete,Complete,149,N/A,N/A,Blue
P5,P5,N/A,Complete,8229781469,Complete,Complete,1970108556,1458221526,Complete,Complete,135,N/A,N/A,N/A
P6,P6,6/10/86,Complete,9993459610,N/A,N/A,N/A,8932757305,6397254206,Complete,Complete,107,62,25,N/A
P7,P7,6/14/00,Complete,1057958413,Complete,N/A,5774440050,N/A,N/A,N/A,135,N/A,2,N/A
P8,P8,N/A,Complete,1098295438,N/A,Complete,0561170035,7981797408,Complete,Complete,236,N/A,N/A,Green
P9,P9,3/27/36,Complete,2148491160,N/A,Complete,7901815542,3054290177,Complete,Complete,204,70,75,N/A
P10,P10,N/A,Complete,7198293807,Complete,Complete,7110963024,8148585368,Complete,Complete,274,83,N/A,Red
P11,P11,11/26/04,Complete,N/A,Complete,N/A,7505898530,7371637729,Complete,Complete,327,59,7,N/A
P12,P12,1/2/02,Complete,6026380182,Complete,Complete,1723363281,7362707738,Complete,N/A,270,N/A,9,Orange
P13,P13,11/2/79,N/A,N/A,Complete,Complete,2082307399,N/A,Complete,Complete,114,70,32,Violet
P14,P14,9/29/96,Complete,7558042144,Complete,Complete,8966736543,1509144199,N/A,Complete,322,N/A,15,Red
P15,P15,6/21/08,N/A,Complete,1828723454,Complete,Complete,4672767433,N/A,Complete,Complete,245,N/A,13,Violet
P16,P16,9/5/01,Complete,2535132609,Complete,Complete,N/A,4725248219,Complete,Complete,200,82,10,Violet
P17,P17,3/3/77,Complete,4112521449,Complete,Complete,

Fig. 4

```
Result Print Out:
PDS using user IMs is: 83.44624910265614
PDS using balanced IMs is: 82.41200030150792
No PSS generated.
No DFCs with subgroup generated.

RSS for each entry as follows:
Last Name: P1   First Name: P1    RSS: 78.5714285714285714
Last Name: P2   First Name: P2    RSS: 86.6071428571428571
Last Name: P3   First Name: P3    RSS: 83.9285714285714286
Last Name: P4   First Name: P4    RSS: 67.4107142857142857
Last Name: P5   First Name: P5    RSS: 74.5535714285714286
Last Name: P6   First Name: P6    RSS: 82.1428571428571429
Last Name: P7   First Name: P7    RSS: 62.9464285714285714
Last Name: P8   First Name: P8    RSS: 75.4464285714285714
Last Name: P9   First Name: P9    RSS: 90.1785714285714286
Last Name: P10  First Name: P10   RSS: 82.1428571428571429
Last Name: P11  First Name: P11   RSS: 79.4642857142857143
Last Name: P12  First Name: P12   RSS: 88.8392857142857143
Last Name: P13  First Name: P13   RSS: 81.25
Last Name: P14  First Name: P14   RSS: 88.8392857142857143
Last Name: P15  First Name: P15   RSS: 86.1607142857142857
Last Name: P16  First Name: P16   RSS: 85.5357142857142857
Last Name: P17  First Name: P17   RSS: 100.0
Last Name: P18  First Name: P18   RSS: 88.8392857142857143
Last Name: P19  First Name: P19   RSS: 71.875
Last Name: P20  First Name: P20   RSS: 72.3142857142857143
```

Fig. 9

```
 result.txt

Last Name:    P195    First Name:    P195    RSS: 80.0
Last Name:    P196    First Name:    P196    RSS: 60.0
Last Name:    P197    First Name:    P197    RSS: 86.66666666666667
Last Name:    P198    First Name:    P198    RSS: 86.66666666666667
Last Name:    P199    First Name:    P199    RSS: 93.33333333333333

DFCS for each field is as follows::
Last Name:     100.0
First Name:    100.0
DoB:           78.89447236180904
Address:       83.41708542713567
Phone #:       81.90954773869346
Email:         79.89949748743719
Ins Co:        80.40201005025126
Ins Group #:   83.41708542713567
Ins Policy #:  79.39698492462311
Med History:   77.38693467336684
Allergies:     76.88442211055276
Weight:        80.40201005025126
Height:        71.85929648241206
Age:           78.89447236180904
Race:          83.41708542713567

End of Report
```

Fig. 10

```
Result Print Out:
PDS using user IWs is:  91.36931719965415
PDS using balanced IWs is:  34.51520270270266
No PSS generated.
No DFCS with subgroup generated.
```

Fig. 13

METHOD AND SYSTEM FOR MANAGING HEALTH CARE PATIENT RECORD DATA

RELATED APPLICATION DATA

The instant application claims priority to U.S. provisional application 62/234,792 filed Sep. 30, 2015, the subject matter of which is incorporated by reference in its entirety.

BACKGROUND OF THE INVENTION

Field of the Invention

The present invention is directed to methods and systems for managing health care patient record data by evaluating the strength and completeness of patient record data stored in health care/medical databases through determining the existence and relative quality of such data and performing statistical analyses.

Description of the Related Art

As health care moves into the 21st century, practitioners are moving into an era where traditionally qualitative methods of care are being complemented with quantitative research and analysis to better understand and solve various problems. To that end, one important problem health care practices currently face is the strength of their patient records and databases. While electronic records of patient information and care are now prevalent throughout health centers across the United States, there are few systems in place to ensure the completeness and validity of patient record data being stored. From basic information such as phone numbers or email addresses to more involved information such as family history and procedure records, there is no centralized mechanism by which data entered by health care staff can be checked for completeness and validity. Furthermore, there are no centralized mechanisms by which various health care software database packages and health center record-keeping measures can be compared to determine advantages and disadvantages of different systems.

Without having a mechanism that can identify strengths and shortcomings in record-keeping procedures it becomes more difficult to ensure the highest standard of care across health care centers. Most importantly, these problems are being uncovered at a time where data accuracy in health care is becoming a cornerstone for the burgeoning field of health informatics as well as a fundamental part of new models of health care practice. Accordingly, there is a continued need in the art for methods and systems that can identify strengths and shortcomings in record-keeping procedures for health care patient record data for the purpose of better and more accurate management of the patient record data. There is also a need for such a system that is independent of the health care platform used to store patient record data so that the system may be implemented by all health care providers across all health care platforms.

Database completeness information is also useful to identify health care disparities. The Department of Health and Human Services (DHHS) has found overwhelming evidence of healthcare disparity in minority groups, including disparities in care for cancer, cardiac disease, AIDS, asthma, and other illnesses. Research further shows that racial and ethnic disparities in health care exist even when insurance status, income, age, and severity of conditions are comparable. There is also evidence in health care decision making at multiple levels of bias against individuals based on age, creating health care disparity for the elderly. From a gender perspective, differences in health care expenditures and resource utilization lead to better quality of care among females. The underlying sources for these disparities are hard to identify. For example, a physician's assumption of literacy among patients disproportionately impacts minority patients, becoming a factor leading to disparity in care.

Research also points to social sources outside of interactions within the health care provider environment (such as neighborhood pressures, socioeconomic circumstances, education, segregation, impact on income, violence, and impact of segregation) contributing to real disparities in health care provided to minorities. These factors, often embedded and persistent historically, complicate the ability to determine tangible sources of disparities, ability to measure these sources' effects, and ability to create effective solutions to these sources of disparities. Within the provider context, "barriers in the patient-physician relationship contribute to racial disparities in the experience of health care." Furthermore, prejudice, clinical uncertainty (e.g. different interpretations of symptoms from minority patients), and stereotyping contribute as sources of health care disparity within the medical environment.

Analyzing patient record data in terms of variance between subpopulations is important clinically to determine areas of incomplete information and finding asymmetries that can be attributed to disparities in delivery of care. Current systems do not address the collection and maintenance of health care data with regard to identifying underlying disparities among various subpopulations, such as those based on age, gender, and race. Therefore, current systems fail at identifying and correcting underlying systemic issues causing these disparities. Accordingly, there is a need for a system that can identify variances in health care record completeness among subpopulations.

Description of the Related Art Section Disclaimer: To the extent that specific patents/publications/products are discussed above in this Description of the Related Art Section or elsewhere in this Application, these discussions should not be taken as an admission that the discussed patents/publications/products are prior art for patent law purposes. For example, some or all of the discussed patents/publications/products may not be sufficiently early in time, may not reflect subject matter developed early enough in time and/or may not be sufficiently enabling so as to amount to prior art for patent law purposes. To the extent that specific patents/publications/products are discussed above in this Description of the Related Art Section and/or throughout the application, the descriptions/disclosures of which are all hereby incorporated by reference into this document in their respective entirety(ies).

SUMMARY OF THE INVENTION

The disclosure is directed to inventive methods and systems for managing health care patient record data by evaluating the strength and completeness of patient record data stored in health care/medical databases through determining the existence and relative quality of such data and performing statistical analyses. An embodiment can include, but is not limited to, a method and system that is configured to (i) associate native health care patient record data of at least a first patient representing the first patient's health care record stored in a database to a plurality of data fields (or other type of organization), and examine the patient record data associated with the particular fields, (ii) assign a relative importance weight score to each of the plurality of data fields representing the first patient's health care patient record data, and (iii) generate statistical results that can be used to determine the completeness of individual patient record data as well as the general thoroughness of record keeping in a medical database. An embodiment can use a component that can be customized to the settings of the particular software package used for storing the patient record data, as well as a Comma Separated Values (CSV) file parser to develop and read concept maps.

Such a system (or tool), along with its various embodiments, can be called the Data Completeness Analysis Package (DCAP), which is a term used in this disclosure. This tool can either reside on an individual workstation or an accessible server, each of which can be separate from and/or directly connected to a health care database (and can also reside on a health care database itself). This tool was developed based on the following objectives: develop a tool that can be used alongside and be compatible with a variety of health care database software packages to automatically determine the completeness of individual patient records as well as aggregate patient records across health care centers and subpopulations; equip the tool with robust statistical analysis techniques to ensure that the importance of the various types of data is accounted for; and make the tool user friendly for health care staff to evaluate the strength of record-keeping. Based on these objectives, the tool created was successful in applying the statistical techniques evaluated and described in this disclosure, and was able to evaluate the strength of an actual health care database (specifically, the HCUP SID Florida database), as described below.

According to an aspect, a method for managing health care patient record data includes the steps of: associating, by a processor, native health care patient record data of a first patient stored in a database to a plurality of data fields, wherein the native health care patient record data of the first patient represents the first patient's health care record; assigning, by a processor, a relative importance weight score to each of the plurality of data fields; and generating, by a processor, a record strength score of the first patient's health care record based on the relative importance weight score assignments.

According to an embodiment, the step of generating further comprises the step of determining a record strength score pursuant to the following formula:

$$RSS\ (\%) = \frac{(IW_1)(X_1) + (IW_2)(X_2) + (IW_3)(X_3) + \ldots + (IW_n)(X_n)}{\sum_{i=1}^{n} IW_i} \times 100$$

where RSS=record strength score (total strength of completeness for the first patient's health care record constrained from 0 to 100%); IWi=importance weight of $i^{th}$ data field; and Xi=binary completeness variable for $i^{th}$ data field (1 represents complete data field, 0 represents incomplete).

According to an another aspect, a non-transitory computer-readable storage medium containing program code includes: program code for associating native health care patient record data of a first patient stored in a database to a plurality of data fields, wherein the native health care patient record data of the first patient represents the first patient's health care record; program code for assigning a relative importance weight score to each of the plurality of data fields; and program code for generating a record strength score of the first patient's health care record based on the relative importance weight score assignments.

According to an embodiment, the program code for generating further comprises program code for determining a record strength score pursuant to the following formula:

$$RSS\ (\%) = \frac{(IW_1)(X_1) + (IW_2)(X_2) + (IW_3)(X_3) + \ldots + (IW_n)(X_n)}{\sum_{i=1}^{n} IW_i} \times 100$$

where RSS=record strength score (total strength of completeness for the first patient's health care record constrained from 0 to 100%); $IW_i$=importance weight of $i^{th}$ data field; and $X_i$=binary completeness variable for $i^{th}$ data field (1 represents complete data field, 0 represents incomplete).

In accordance with a particularly advantageous aspect, a specialized improved computer system is created as described herein—here the devices, databases and/or systems that are specifically structured, configured, connected, and/or programmed to evaluate the strength and completeness of patient record data stored in health care/medical databases through determining the existence and relative quality of such data and performing statistical analyses.

The transmission/transfer of data to/from systems, databases, engines, mobile devices, or other computer based devices/systems described in this disclosure can be via wireless communication/transmission over a network, which can be any suitable wired or wireless network capable of transmitting communication, including but not limited to a telephone network, Internet, Intranet, local area network, Ethernet, online communication, offline communications, wireless communications and/or similar communications means. The wireless transmission can be accomplished through any wireless protocol/technology, including, but not limited to, ZigBee standards-based protocol, Bluetooth technology, and/or Wi-Fi technology. Further, this data can be encrypted as needed based on the sensitivity of the data or the location the database with respect to a mobile device, for example. One system can be located in the same room, in a different room in the same building, in a completely different building and location from another system, or in the "cloud." The storage of the data in the cloud can be subject to security measures, as should be appreciated by those of skill in the art. Various alerts and notifications can be sent to authorized users of the systems described herein by the data transmission means described herein or as may be known or appreciated by those of skill in the art.

The details of one or more embodiments are described below and in the accompanying drawings. Other objects and advantages of the present invention will in part be obvious, and in part appear hereinafter.

BRIEF DESCRIPTION OF THE DRAWINGS

The present invention will be more fully understood and appreciated by reading the following Detailed Description in conjunction with the accompanying drawings. The accompanying drawings illustrate only typical embodiments of the disclosed subject matter and are therefore not to be considered limiting of its scope, for the disclosed subject matter may admit to other equally effective embodiments.

Reference is now made briefly to the accompanying drawings, in which:

FIG. 4 is a representation of a sample CSV document in accordance with an embodiment.

FIG. 9 is a representation of a hypothetical patient DCAP result part 1 document in accordance with an embodiment.

FIG. 10 is a representation of a hypothetical patient DCAP result part 2 document in accordance with an embodiment.

FIG. 13 is a representation of results of HCUP data for unbalanced IWs document in accordance with an embodiment.

Figure 1:
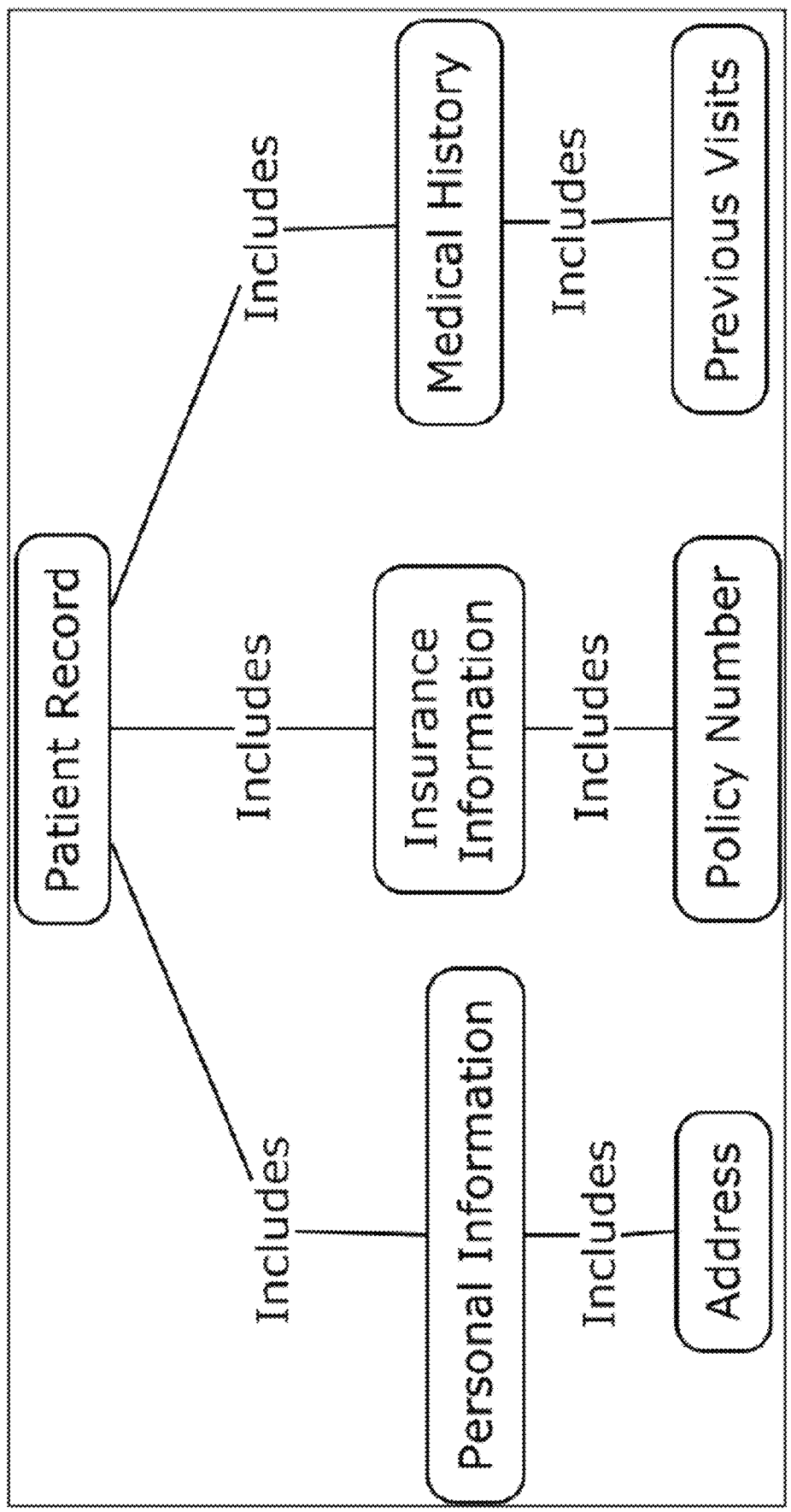
FIG. 1 is a schematic representation of a top level patient concept map in accordance with an embodiment.

Where applicable, like reference characters designate identical or corresponding components and units throughout the several views, which are not to scale unless otherwise indicated. Moreover, the embodiments disclosed herein may include elements that appear in one or more of the several views or in combinations of the several views.

DETAILED DESCRIPTION

The present invention will be more fully understood and appreciated by reading the following Detailed Description in conjunction with the accompanying drawings, wherein like reference numerals refer to like components.

As detailed herein, the present disclosure is directed to embodiments of a method and system for managing health care patient record data by evaluating the strength and completeness of patient record data stored in health care/medical databases through determining the existence and relative quality of such data and performing statistical analyses. As part of the proof of concept of embodiments described herein, but in no way limiting the embodiments described herein in any way, health care patient record data can be transformed into concept maps and these maps can be used as the basis for thorough statistical analysis. Concept maps are visual representations of data stored in a system, traditionally used for expressing knowledge in both a declarative and procedural sense. While most concept mapping tools have been used to express knowledge in a teaching environment to evaluate student learning of various topics, for the purposes of this disclosure, concept mapping is used as a schema through which patient record data stored could be represented and uniformly examined independent of the platform the data was originally stored on or other health care protocols that may make cross examinations of data sets more difficult. These concept maps can be developed through DCAP and then converted to CSV files. The CSV files can then be analyzed through a parser that allows the user to determine the strength of both individual patient records as well as the strength of record keeping throughout a particular database.

A premise of the proof of concept of the method and system described herein is to use concept maps as a representation of patient record data, although the patient record data can be represented in any manner as may be understood and/or appreciated by one of skill in the art. Referring now to FIG. 1, there is shown a schematic representation of a top level patient concept map in accordance with an embodiment. While traditionally concept maps are used to understand the knowledge set and complexity of a human learner, in the embodiment shown in FIG. 1, concept mapping is applied to represent patient information. This patient concept map is generated using data stored in the health care database and mapped using a user-developed 'master map'.

Figure 2:
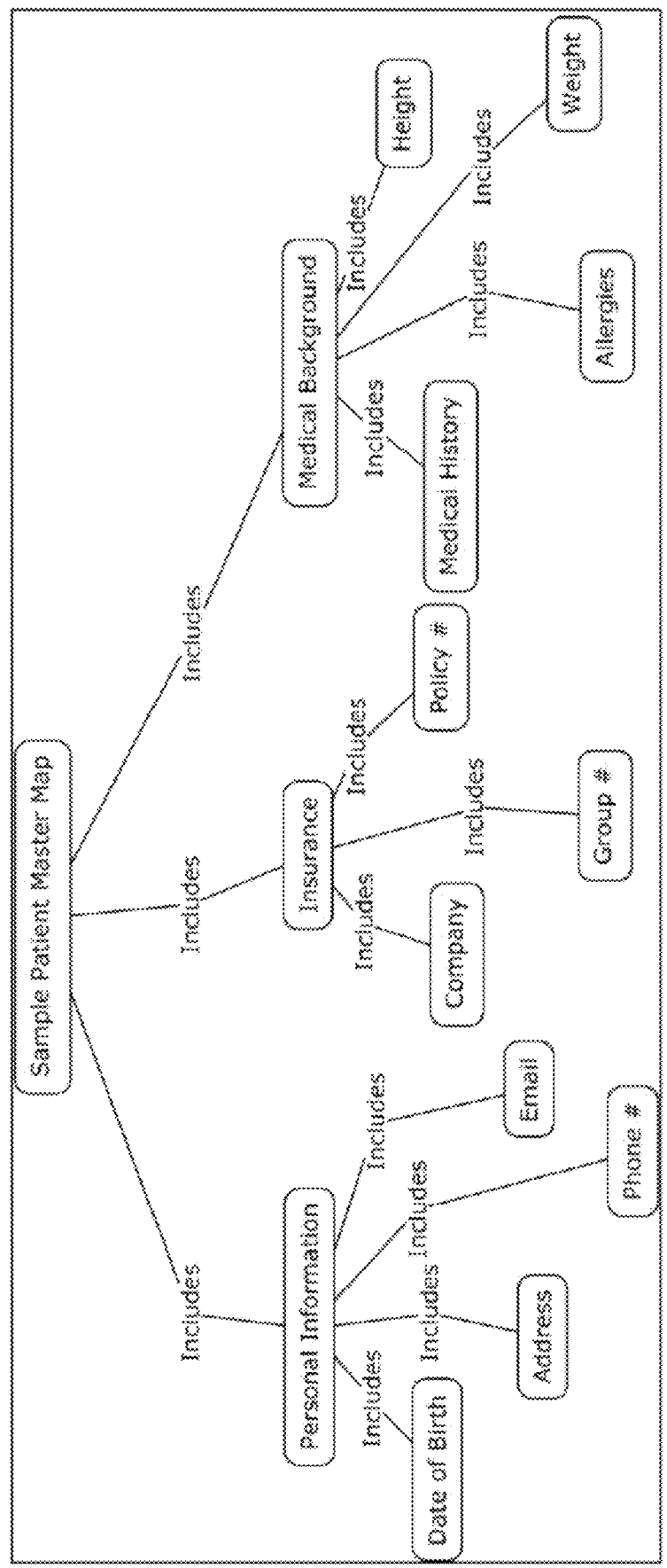
FIG. 2 is a schematic representation of a patient master map in accordance with an embodiment.

Referring now to FIG. 2, there is shown a schematic representation of a patient master map in accordance with an embodiment. In FIG. 2, the master map is a schema that represents all the information, both the data fields and the proper interconnectedness amongst those data fields, the way the user wishes them to be stored in order to be considered 'complete'. While among patient records within a health care center this master map may be constrained by the database software used or methods of patient data recording used by staff, when comparing data sets from various health care centers using DCAP, the master map can be broadened as may be desired or necessary.

Figure 3:
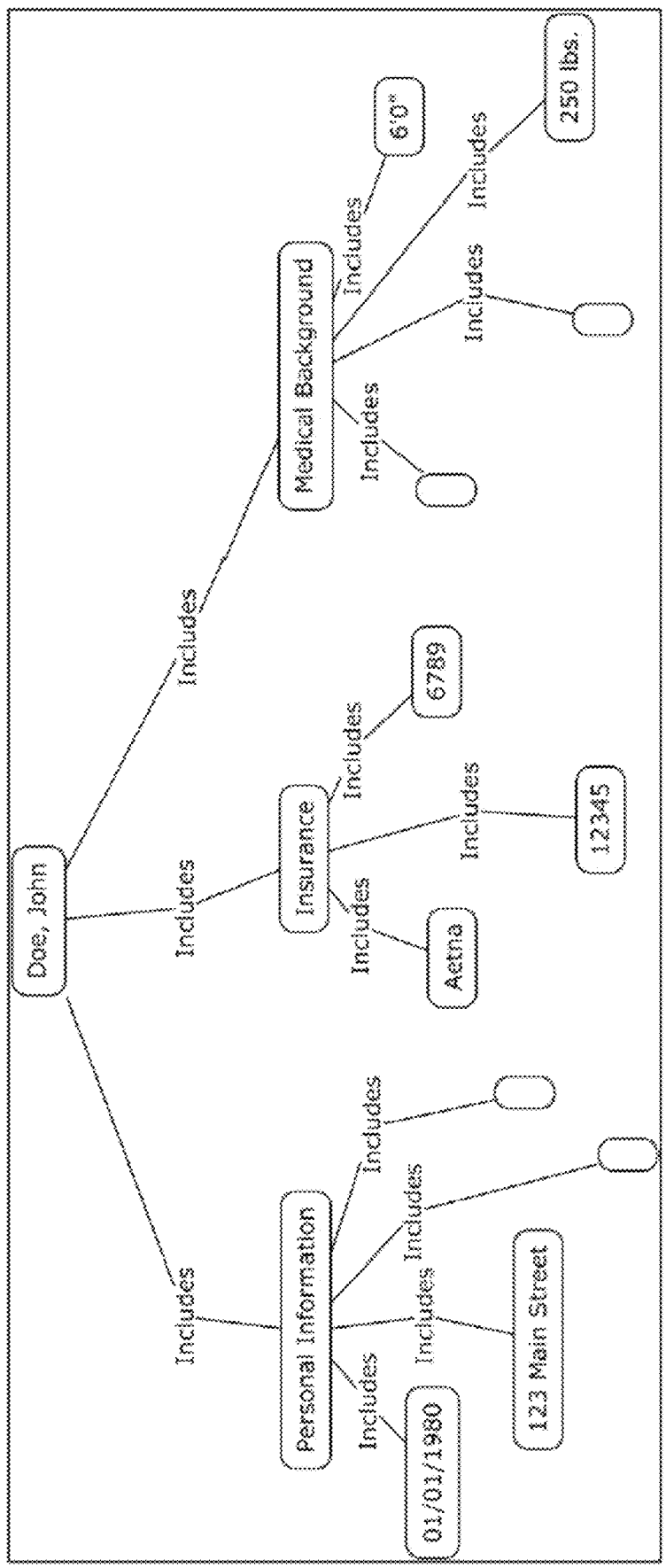
FIG. 3 is a schematic representation of a patient concept map with missing entries in accordance with an embodiment.

Referring now to FIG. 3, there is shown a schematic representation of a patient concept map with missing entries in accordance with an embodiment. The example of the master map shown in FIG. 3, a sample patient concept map with missing entries, i.e., not complete, and the example of a patient master map shown in FIG. 2 highlight how the concept of completeness and subsequently the strength of individual and aggregate patient data can be visualized. While FIGS. 2 and 3 are not comprehensive, they show how uniform concept map representations can serve as a platform through which basic shortcomings in patient data can be understood. It is also important to note that while cross subgroup relationships and other schema complexity may be useful in both traditional educational applications and even patient record applications. For example, address and phone number are concepts that can be linked to both personal information and billing information. For the purposes of this disclosure, having the information as defined by the master map can be sufficient to determine completeness.

Once the native patient data in a particular health care database software package is converted into concept map representations using a template master map, the concept maps are converted into CSV documents. Referring to FIG. 4, a sample CSV document is shown which includes concept labels, i.e., patient data fields. A CSV analyzer then parses the documents to see which fields are filled and unfilled, and then sends its results for statistical analysis. After the relevant statistics have been generated, e.g., individual patient records, entire database completeness, etc., a user-friendly interface system is used to display the results for the user.

Figure 5:
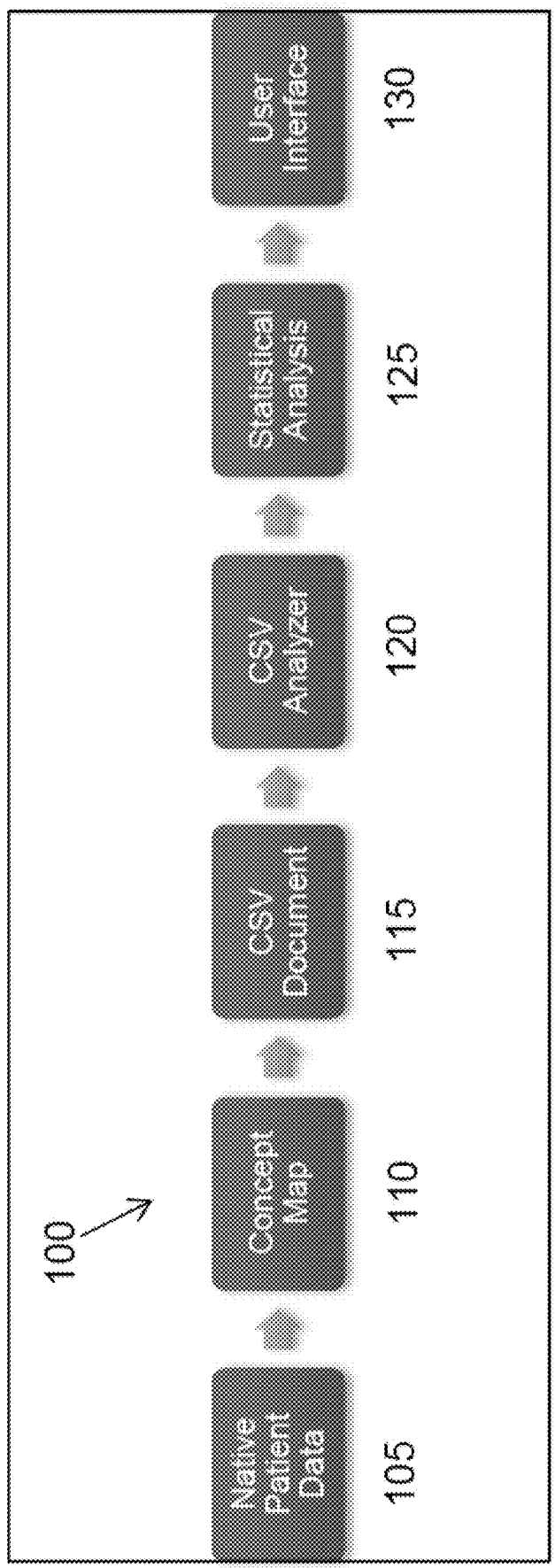
FIG. 5 is a flow chart of a method for managing health care patient record data in accordance with an embodiment.

Referring to FIG. 5, a flowchart of a basic method 100 for managing health care patient record data is provided based on the above description, in accordance with an embodiment. Each of the steps of the method can be carried out by a processor associated with DCAP and programmed/configured to carry out such steps.

Turing to step 105 of method 100, native patient record data is stored in at least one health care database with a particular software package and platform used for storing the patient record data. Other health care databases can exist, which store patient record data, and can include the same or a different software package and platform used for storing the patient record data.

At step 110 of the method 100, a master map is developed that represents all the information, both the data fields and the proper interconnectedness amongst those data fields the way a user wishes them to be stored in order to be considered 'complete'. A concept map of stored native patient data of a particular patient, or concept maps, each of which is associated with particular patients, is generated using the developed master map as a template.

At step 115 of the method 100, each concept map is converted into a Comma Separated Values (CSV) document. This conversion to a CSV document is performed so that, at step 120 of the method 100, a CSV analyzer can analyze and parse the CSV document(s) to determine which data fields are filled and unfilled. At step 125 of the method 100, the results of the CSV analysis are statistically analyzed. At step 130 of the method 100, results of the statistical analysis are generated and transmitted and displayed to a user on any mobile or non-mobile computing device, for example. Further details of the statistical analysis are set forth in further detail below.

Advantages of embodiments, as briefly detailed above and shown in the Figures, are illustrated by the following Exemplary System, Uses and Functionalities description. However, the particular components, uses, functionalities and amounts thereof recited in this description, as well as other conditions and details, are to be interpreted to apply broadly in the art and should not be construed to unduly restrict or limit the invention in any way.

In accordance with an exemplary embodiment, once the patient data has been processed by the CSV analyzer or otherwise is associated with a plurality of data fields or other organization means, DCAP is programmed and/or configured to implement statistical analysis in order to determine the completeness and strength of the patient data. While completeness in each individual data field can be identifiable by the presence or lack of data, holistically analyzing an individual patient's record or an entire database or subgroup of patients can require determining which data fields are more important than others. With this in mind, DCAP generates a Record Strength Score (RSS) that is based upon user and/or computer determined input of Importance Weights (IW).

To illustrate this concept, a first example is a scenario where each data field holds an equivalent importance and thus equivalent IWs. A second example is a scenario where the IWs are different. For the scoring itself, each IW ranges from 1 to 100 points, with 100 denoting maximum importance. However, any number range can be used. For a record with all data fields of equivalent importance, 100 points are used for each data field. It is also important to note that while the concept map shows various grouping concepts that organizes the data fields, such as 'personal information', 'insurance', or 'medical background', these groupings have no scoring. Thus, the only scoring concepts are those with actual corresponding data fields. The scoring equation is as follows:

$$RSS(\%) = \frac{(IW_1)(X_1) + (IW_2)(X_2) + (IW_3)(X_3) + \ldots + (IW_n)(X_n)}{\sum_{i=1}^{n} IW_i} \times 100 \quad (1)$$

where RSS=Record Strength Score (Total Strength of Completeness for Individual Patient Record constrained from 0 to 100%); $IW_i$=Importance Weight of $i^{th}$ data field; $X_i$=Binary Completeness Variable for $i^{th}$ data field (1 represents complete data field, 0 represents incomplete).

Figure 6:
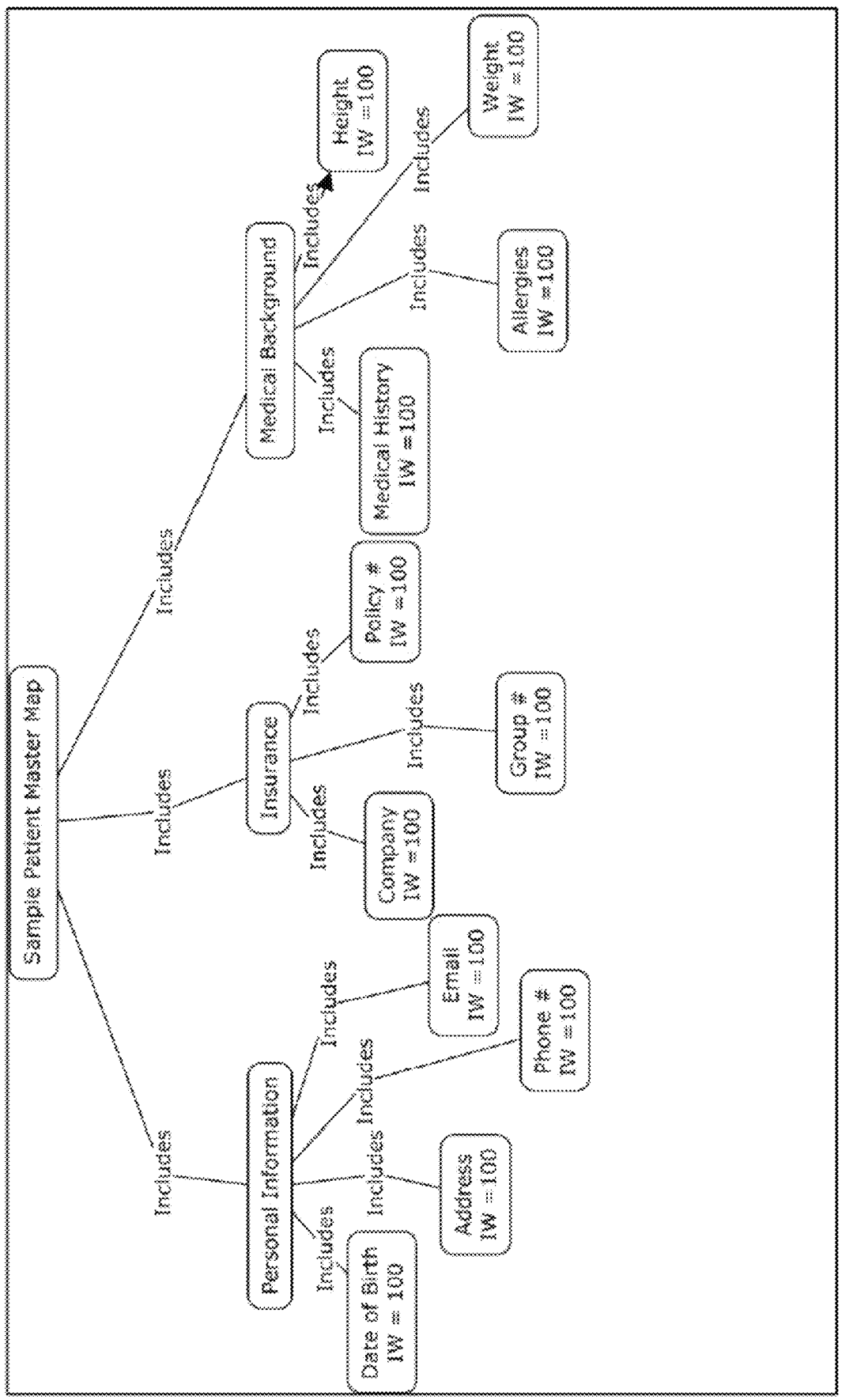
FIG. 6 is a schematic representation of a patient master map with balance scoring in accordance with an embodiment.
Figure 7:
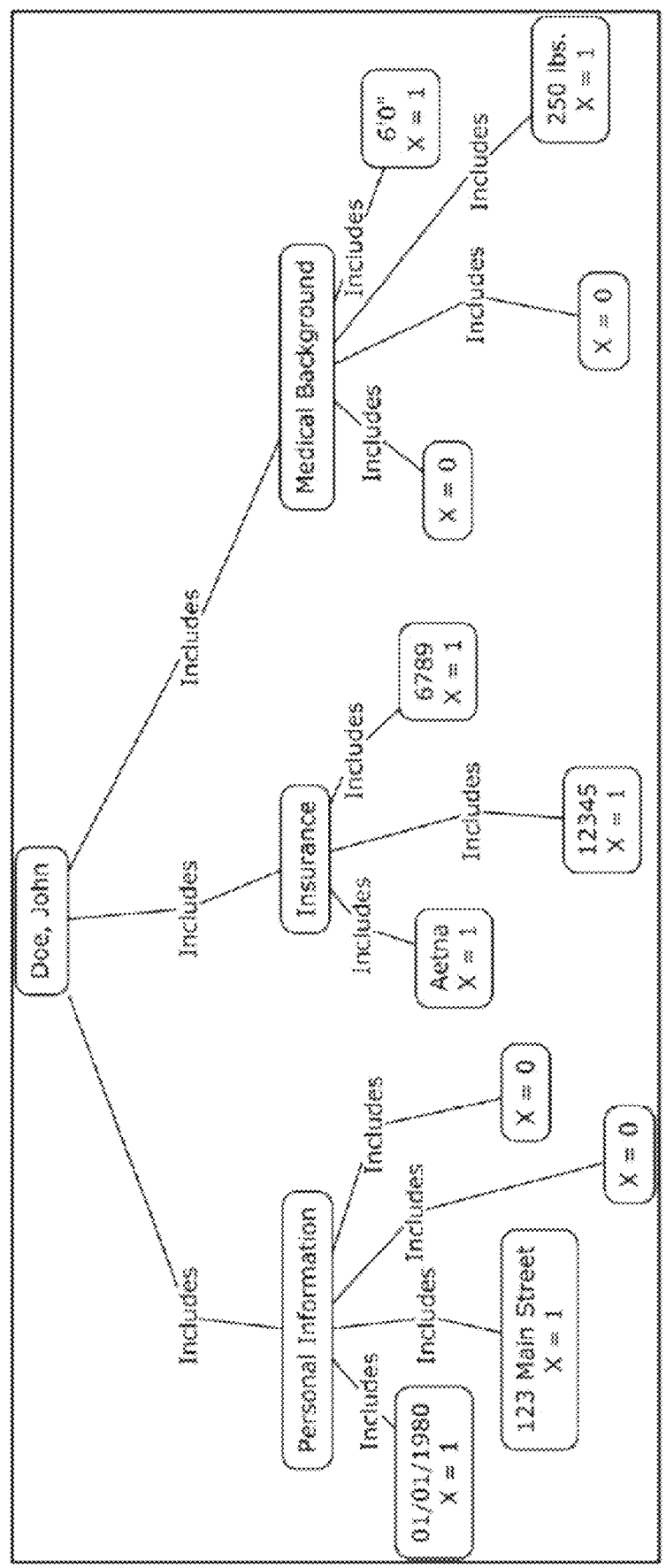
FIG. 7 is a schematic representation of a patient master map with balance scoring in accordance with an embodiment.

Turning to FIG. 6, a sample patient master map for balanced scoring is shown, in accordance with an embodiment. FIG. 7 follows with the sample patient map indicating the Binary Completeness Variable for each field, in accordance with an embodiment. Based on those maps and the scoring equation, the RSS for the sample patient is 64%.

Figure 8:
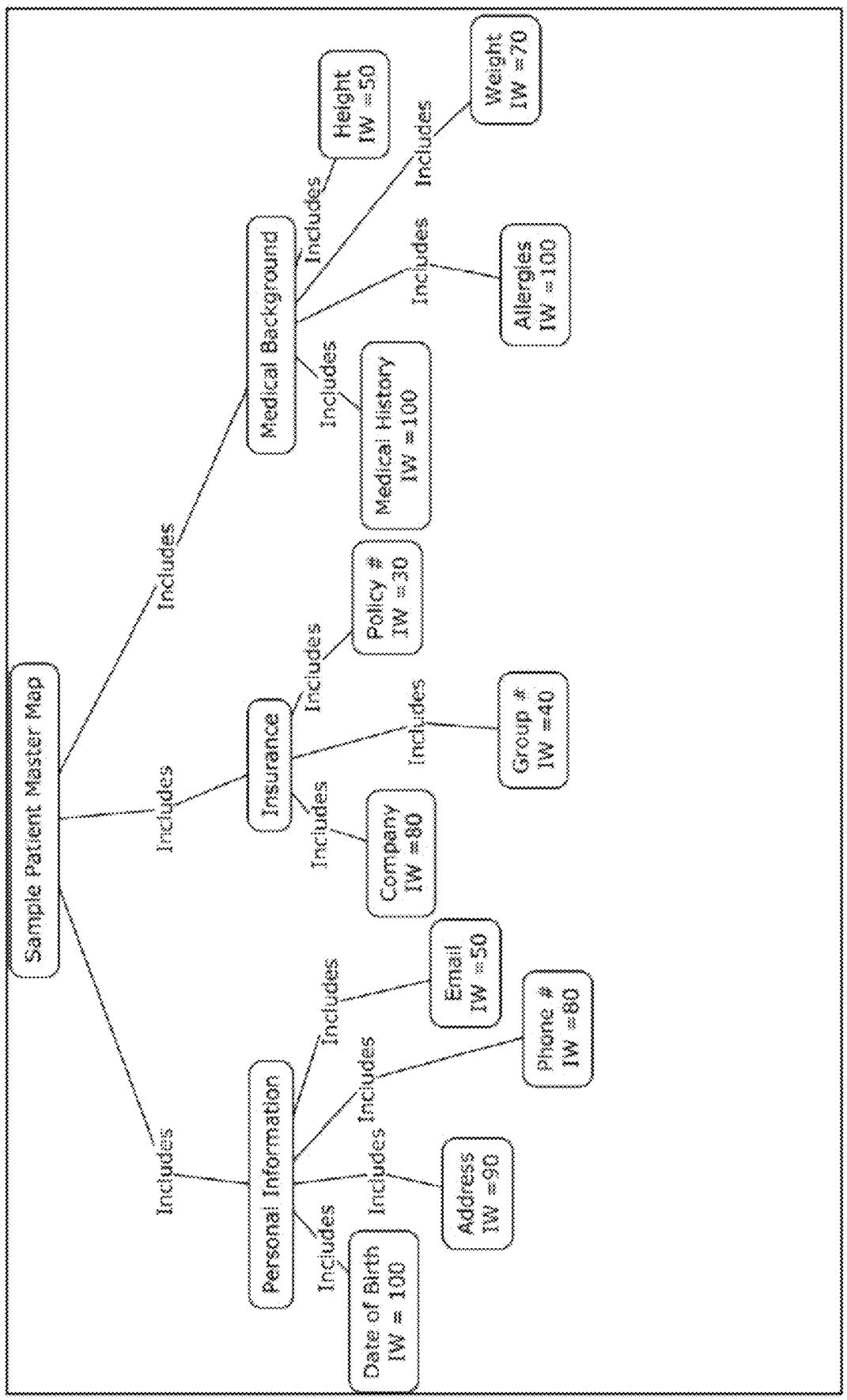
FIG. 8 is a schematic representation of a patient map with balance scoring in accordance with an embodiment.

Table 1, shown below, illustrates IWs for an unbalanced RSS, and FIG. 8 shows the new sample patient master map with modified unbalanced IWs, while the Binary Completeness Variables for the sample patient shown in FIG. 7 remain unchanged, in accordance with an embodiment. The weights used are for purposes of example and have no bearing on actual or perceived relative importance of data fields. Based on those maps and the scoring equation, the RSS for the sample patient is 58%, showing that these new unbalanced IWs make this patient record 'less complete'.

TABLE 1

Unbalanced Importance Weights for Sample Patient

| Data Field | Importance Weight |
| --- | --- |
| Date of Birth | 100 |
| Address | 90 |
| Phone # | 80 |
| Email | 50 |
| Insurance Company | 80 |
| Insurance Group # | 40 |
| Insurance Policy # | 30 |
| Medical History | 100 |
| Allergies | 100 |
| Weight | 70 |
| Height | 50 |

While there appears to be no certain answer for an optimal scoring algorithm that can take into account various preferences for the importance of individual patient record data fields, implementing the RSS scoring equation in DCAP allows for the score to be tailored to the needs of the user because it is dynamic and modifiable. Further development and use of DCAP can also lead to discoveries in better scoring algorithms, and the possibilities with those improvements are elaborated upon later in this disclosure.

Another important metric to establish is the Patient Database Score (PDS), which defines the overall strength of all records in the database and is the average of the various RSS scores (Equation 2). This metric allows for comparisons between databases to determine better record keeping software packages and strategies. Furthermore, using database segmentation techniques, subpopulations of patient records can be compared using the Patient Subgroup Score (PSS), which averages the RSS scores of the patients of interest by age, race, gender, and insurance status, for example, and can allow for an in depth analysis of record strength based on patient information (Equation 3). This topic is further elaborated upon later in this disclosure.

$$PDS(\%) = \frac{RSS_1 + RSS_2 + \ldots + RSS_n}{n} \quad (2)$$

where $RSS_i$=Record Strength Score (Total Strength of Completeness for Individual Patient Record constrained from 0 to 100%) for $i^{th}$ patient; and n=Total number of patient records.

$$PSS(\%) = \frac{RSS_1 + RSS_2 + \ldots + RSS_n}{n} \quad (3)$$

where $RSS_i$=Record Strength Score (Total Strength of Completeness for Individual Patient Record constrained from 0 to 100%) for $i^{th}$ patient that meets subpopulation condition; and n=Total number of patient records that meet subpopulation condition.

Individual data fields across the patient database can also be compared using the Data Field Completeness Score (DFCS), which averages the binary completeness variable of a specific data field across all (Equation 4), or a subgroup of (Equation 5), patients to determine how well one particular class of data is being recorded. The DFCS allows for comparisons across databases and subgroups to ensure proper patient record keeping for each data field. The various scores and terms of importance in scoring are summarized in Table 2, below.

$$DFCS_k(\%) = \frac{\sum_1^n X_{ik}}{n} \times 100 \quad (4)$$

where $X_{ik}$=Binary Completeness Variable for $i^{th}$ patient (1 represents complete data field, 0 represents incomplete) and $k^{th}$ data field, where k remains constant and i iterates for individual patients; and n=Total number of patient records.

$$DFCS_k(\%) = \frac{\sum_1^n X_{ik}}{n} \times 100 \quad (5)$$

where $X_{ik}$=Binary Completeness Variable for $i^{th}$ patient (1 represents complete data field, 0 represents incomplete) and $k^{th}$ data field, where k remains constant and i iterates for individual patients that meet the subpopulation condition; and n=Total number of patient records that meet subpopulation condition.

TABLE 2

Summary of Various Scores Produced by DCAP

| Metric | Definition | Discription | Example |
|---|---|---|---|
| Record Strength Score (RSS) | See Equation 1 | Measures the strength of an individual patients record | Mr. John Doe's record has a 70% RSS score |
| Patient Database Score (PDS) | See Equation 2 | Measures the strength of the entire patient record database at a health care center | XYZ Medical Center's PDS Score is 50% |
| Patient Subgroup Score (PSS) | See Equation 3 | Measures the strength of the patient records of a specific population of the patients seen by the health care center | The PSS Score of male patients over the age of 55 is 95% |
| Data Field Completeness Score (DFCS) | See Equation 4 for database See Equation 5 for subpopulation | Measures the strength of recording for a specific data field for either all patients in a database or a subset of patients | The DFCS for Insurance Policy Number is 80% The DFCS for height among females is 86% |

Experimentation—Experimenting with Hypothetical Data

In order to build and test DCAP, first a random population set was generated in Excel® using the same fields as shown in FIGS. 2 and 3. The Excel random function was used to introduce random missing fields and the file was converted into a CSV format to be used by DCAP. In terms of specific mechanics of a DCAP embodiment itself, DCAP is programmed and/or configured to read in three CSV files: (1) Patient File—These are each of the patients records in one CSV, with columns representing fields and rows representing individual patients; (2) Template File—These are all of the field labels (one row with multiple columns matching in order to the fields stored in the patient file); and (3) Importance Weight File—These are the importance weight corresponding to the template file.

DCAP is then programmed and/or configured to take these files, convert them to arrays, check for completeness against a defined String variable that indicates incompleteness which can range from a first character indicator to a blank value, and then output the general result of the PDS for the entire database and RSS for each patient. Each of the metrics, PDS and RSS, are also calculated for balanced IWs so that one can compare a simple average to the average weighted by user IWs in the Importance Weight file. DCAP is also programmed and/or configured to automatically generate the DFCS for each field. FIGS. 9 and 10 show samples of this DCAP result printout, with FIG. 9 showing a sample hypothetical patient DCAP result part 1 and FIG. 10 showing a sample hypothetical patient DCAP result part 2.

Figure 11:
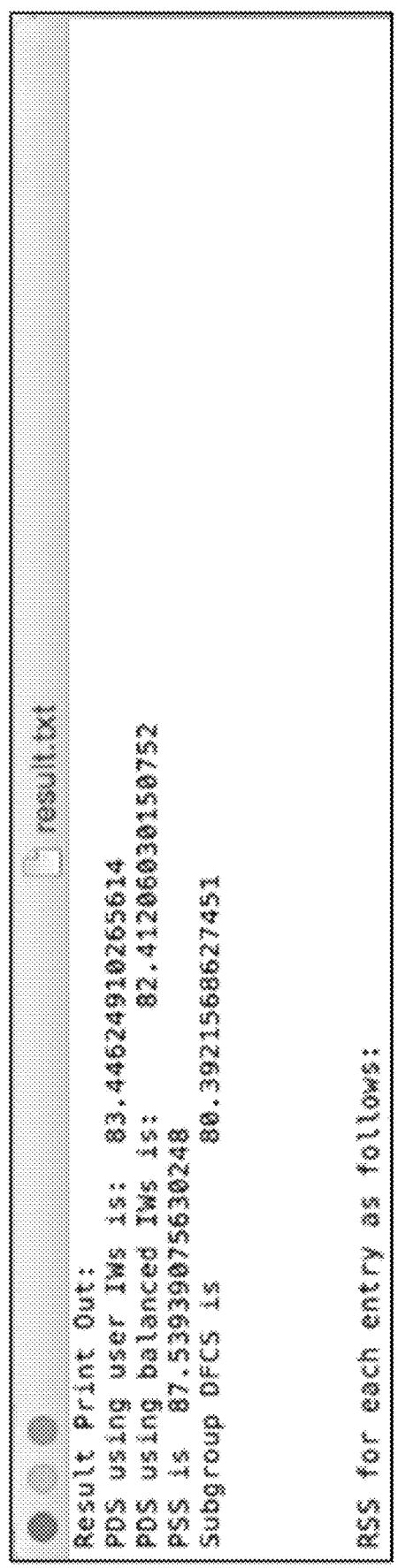
FIG. 11 is a representation of a patient result from hypothetical data with PSS and subgroup DFCS scores document in accordance with an embodiment.

Another aspect of DCAP involves further user input to generate PSS scores and subfield DFCS scores. First, after DCAP has generated the data mentioned previously, it can be programmed and/or configured to ask a user whether they would like to generate a PSS or subfield DFCS score. If yes, the user can then select a field and then indicate whether the search inside the field will be an exact text bound or a numerical range. In the case of text bound, patients that will meet the population criteria must have an exact match to the subfield name. For numerical bound, patients that meet the population criteria must be within the lower and upper bound as indicated by the user. Upon specifying the population of interest's parameters, DCAP can be programmed and/or configured to generate the PSS for this subpopulation. It will then be programmed and/or configured to ask the user whether they would like a DFCS score for that subpopulation. If yes is selected, DCAP will be programmed and/or configured to ask for the field and then the DFCS for that subpopulation will generate. FIG. 11 provides a sample patient result for the hypothetical data where PSS and subgroup DFCS were generated. The subpopulation for the sample shown in FIG. 11 includes patients between the age of 0 and 50 and the DFCS field is race.

In order to test DCAP on real patient data, de-identified data from the Healthcare Cost and Utilization Project (HCUP) was used, specifically the State Inpatient Database (SID) with 2012 data from Florida.

Due to the size of the data set, over 2 million entries, one thousand records were randomly extracted in order to test DCAP. Incomplete or missing data was determined based on the guide provided by HCUP data, usually blank spaces in the CSV file. In setting the importance weights, it was noted that many fields were used to handle excess information. For example, there are 31 fields for up to 31 diagnoses, so having a blank in some of those fields is not actually resultant of missing information; therefore, the IWs were adjusted to 0. Otherwise, importance weights were set first to balanced and then based on general view of importance. Due to the large number of data variables contained in the HCUP data, the IWs have been omitted for practical purposes.

Figure 12:
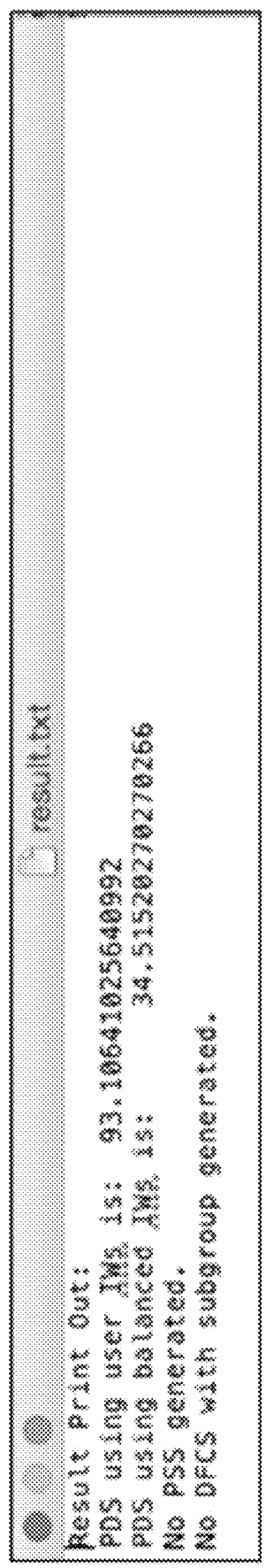
FIG. 12 is a representation of results of HCUP data for balanced IWs document in accordance with an embodiment.

Turning to FIGS. 12 and 13, the results of the HCUP data for the balanced IWs and unbalanced IWs respectively, are shown in accordance with an embodiment. The PDS generated with 'balanced IWs' in the result print out incorporates fields as mentioned above such as multiple diagnosis codes, and thus are not a good measure of record completeness. This simple analysis of HCUP SID data in Florida shows that (1) data is not complete to a level necessary for proper recording of healthcare service, and (2) when the importance of various fields are taken into consideration that measure becomes even weaker. This data and the functionality provided by DCAP allows for multiple areas of further exploration that are discussed later in this disclosure.

Suggestions and Potential Areas of Further Investigation

The issue of automated veracity of patient health care data could be investigated through common data heuristics or through communication with a central database as a cross-reference. Furthermore, IWs can be made less subjective and more objective based on a panel of health professionals to ensure that the completeness of a database is an objective measure based on widely agreed upon standards.

More work can also be done in the area of subpopulation completeness, and public databases such as the HCUP data provide additional data to answer questions of health care record keeping as it pertains to vulnerable populations. Further research and analysis can also be conducted in automating concept map building within DCAP for users and health care personnel to better visualize data and understand the relative importance of different data elements. Patient record strength, completeness, and veracity can ultimately be linked to discrete health care outcomes issues, such as various diagnoses codes, rates of injury, length of care, mortality, etc.

Limitations in access to current clinical data stored in proprietary software packages led to lack in actual testing against various healthcare databases, but the DCAP tool provides promise in its adaptability to various data sets and data elements. Overall, this disclosure describes the use of real data to show the current problem of incomplete patient data and the importance of creating systems to ensure a high standard of data completeness. In its development and limitations it also builds a foundation to explore further areas of interest and advocates work committed to making sure that important patient data is complete and accurate.

A "module," as may be used herein, can include, among other things, the identification of specific functionality represented by specific computer software code of a software program that is recorded on a computer readable medium. A software program may contain code representing one or more modules, and the code representing a particular module can be represented by consecutive or non-consecutive lines of code. The computer-executable program instructions of an embodiment of the present invention can comprise any computer-programming language known in the art, including but not limited to C, Java, Python, Perl, ActionScript and JavaScript, among many others.

As will be appreciated by one skilled in the art, aspects of the present invention may be embodied/implemented as a computer system, method or computer program product. The computer program product can have a computer processor or neural network, for example, which carries out the instructions of a computer program. Accordingly, aspects of the present invention may take the form of an entirely hardware embodiment, an entirely software embodiment, and entirely firmware embodiment, or an embodiment combining software/firmware and hardware aspects that may all generally be referred to herein as a "circuit," "module," "system," or an "engine." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction performance system, apparatus, or device.

The program code may perform entirely on the user's computer, partly on the user's computer, completely or partly on the thermal printer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

The flow diagrams/charts/block diagrams/system architecture diagrams in the Figures illustrate the architecture, functionality, and operation of possible implementations of systems, methods, and computer program products according to various embodiments of the present invention. In this regard, each block in the flowcharts/block diagrams may represent a module, segment, or portion of code, which comprises instructions for implementing the specified logical function(s). It should also be noted that, in some alternative implementations, the functions noted in the block may occur out of the order noted in the figures. For example, two blocks shown in succession may, in fact, be performed substantially concurrently, or the blocks may sometimes be performed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

While embodiments of the present invention have been particularly shown and described with reference to certain exemplary embodiments, it will be understood by one skilled in the art that various changes in detail may be effected therein without departing from the spirit and scope of the invention as defined by claims that can be supported by the written description and drawings. Further, where exemplary embodiments are described with reference to a certain number of elements it will be understood that the exemplary embodiments can be practiced utilizing either less than or more than the certain number of elements.

What is claimed is:

1. A method for managing health care patient record data, the method comprising the steps of:
    providing remote access to a database over a network through a graphical user interface, wherein a user can store health care patient record data in a native format dependent on a software platform used by the user;
    accessing, by one or more processors, the database containing native health care patient record data;
    transforming native health care patient record data of a first patient stored in the database, using the one or more processors, to a standardized format based at least in part on concept mapping in which the first patient's native health care patient record data is converted into a plurality of parsed data fields;
    assigning, by the one or more processors, a relative importance weight score to each of the plurality of data fields, wherein the relative importance weight score is a numerical value corresponding to the relative importance of each of the plurality of data fields;
    generating, by the one or more processors, a numerical record strength score of the first patient's health care record, thereby converting the first patient's health care record from qualitative data to a numerical data set, the record strength determined based on the following formula:

$$RSS(\%) = \frac{(IW_1)(X_1) + (IW_2)(X_2) + (IW_3)(X_3) + \ldots + (IW_n)(X_n)}{\sum_{i=1}^{n} IW_i} \times 100$$

wherein RSS is the record strength score which is a total strength of completeness for the first patient's health care record constrained from 0 to 100%; $IW_i$ is the importance weight of $i^{th}$ data field; and $X_i$ is a binary completeness variable for $i^{th}$ data field wherein 1 represents a complete data field and 0 represents an incomplete data field; and
    displaying on the graphic user interface the numerical record strength score of the first patient's health care record, thereby conveying a quantitative analysis of a completeness of the first patient's health care record.

2. The method of claim 1, further comprising the step of:
    generating, by the processor, a patient database score, wherein the patient database score is an average of record strength scores of all patient health care records in the database;
    wherein the patient database score indicates a percentage of all patient health care records in a database that contains important native health care patient record data.

3. The method of claim 2, wherein the patient database score is generated pursuant to the following formula:

$$PDS(\%) = \frac{RSS_1 + RSS_2 + \ldots + RSS_n}{n}$$

wherein $RSS_i$ is the record strength score which is a total strength of completeness for an individual patient record constrained from 0 to 100% for an $i^{th}$ patient; and n is a total number of patient records in the database.

4. The method of claim 1, further comprising the step of generating, by the processor, a patient subgroup score based on the average of record strength scores of all patient health care records in a subgroup based on a subpopulation condition;
    wherein the patient subgroup score indicates a percentage of all patient health care records in the subgroup that contains important native health care patient record data.

5. The method of claim 4, wherein the patient subgroup score is generated pursuant to the following formula:

$$PSS(\%) = \frac{RSS_1 + RSS_2 + \ldots + RSS_n}{n}$$

wherein $RSS_i$ is the record strength score which is a total strength of completeness for an individual patient record constrained from 0 to 100% for an $i^{th}$ patient that meets the subpopulation condition; and n is a total number of patient records that meet the subpopulation condition.

6. The method of claim 4, wherein the subpopulation condition is selected from a group consisting of age, race, gender, and insurance status.

7. The method of claim 1, further comprising the step of comparing the strength of a selected data field across two or more databases using a data field completeness score based on an average of binary completeness variables of the selected data field in each database;
    wherein the data field completeness score indicates a percentage of all the selected data fields in each database that are complete.

8. The method of claim 7, wherein the data field completeness score is generated for all patients pursuant to the following formula:

$$DFCS_k(\%) = \frac{\sum_1^n X_{ik}}{n} \times 100$$

wherein $X_{ik}$ is a binary completeness variable for an $i^{th}$ patient wherein 1 represents a complete data field and 0 represents an incomplete data field; a $k^{th}$ data field, wherein k remains constant and i iterates for individual patients; and n is a total number of patient records.

9. The method of claim 1, further comprising the step of:
comparing the strength of a selected data field for a subgroup across two or more databases using a data field completeness score based on an average of binary completeness variables of the selected data field in each database;
wherein the data field completeness score indicates a percentage of all the selected data fields in each subgroup of each database that are complete.

10. The method of claim 9, wherein the data field completeness score is generated for a subgroup of patients pursuant to the following formula:

$$DFCS_k(\%) = \frac{\sum_1^n X_{ik}}{n} \times 100$$

wherein $X_{ik}$ is a binary completeness variable for an $i^{th}$ patient wherein 1 represents a complete data field and 0 represents an incomplete data field; a $k^{th}$ data field, wherein k remains constant and i iterates for individual patients that meet a subpopulation condition; and n is a total number of patient records that meet the subpopulation condition.

11. A non-transitory computer-readable storage medium containing program code for executing the following steps:
providing remote access to a database over a network through a graphical user interface, wherein a user can store health care patient record data in a native format dependent on a software platform used by the user;
accessing, by one or more processors, the database containing native health care patient record data;
transforming native health care patient record data of a first patient stored in a database to a plurality of data fields, wherein the native health care patient record data of the first patient represents the first patient's health care record;
assigning a relative importance weight score to each of the plurality of data fields, wherein the relative importance weight score is a numerical value; and
generating a numerical record strength score of the first patient's health care record based on the relative importance weight score assignments, pursuant to the following formula:

$$RSS(\%) = \frac{(IW_1)(X_1) + (IW_2)(X_2) + (IW_3)(X_3) + \ldots + (IW_n)(X_n)}{\sum_{i=1}^n IW_i} \times 100$$

wherein RSS is the record strength score which is a total strength of completeness for the first patient's health care record constrained from 0 to 100%; $IW_i$ is the importance weight of $i^{th}$ data field; and $X_i$ is a binary completeness variable for $i^{th}$ data field wherein 1 represents a complete data field and 0 represents an incomplete data field;
wherein the record strength score indicates a percentage of the first patient's health care record that contains important native health care patient record data; and
displaying on the graphic user interface the RSS of the first patient's health care record, thereby conveying a quantitative analysis of a completeness of the first patient's health care record.

12. The non-transitory computer-readable storage medium of claim 11, further comprising program code for generating a patient database score based on an average of record strength scores; wherein the patient database score indicates a percentage of all patient health care records in a database that contains important native health care patient record data.

13. The non-transitory computer-readable storage medium of claim 12, the patient database score is generated pursuant to the following formula:

$$PDS(\%) = \frac{RSS_1 + RSS_2 + \ldots + RSS_n}{n}$$

wherein $RSS_i$ is a record strength score which is a total strength of completeness for an individual patient record constrained from 0 to 100% for an $i^{th}$ patient; and n is a total number of patient records.

14. The non-transitory computer-readable storage medium of claim 11, further comprising program code for generating a patient subgroup score based on an average of all patient health care records in a subgroup based on a subpopulation condition; wherein the patient subgroup score indicates a percentage of all patient health care records in the subgroup that contains important native health care patient record data.

15. The non-transitory computer-readable storage medium of claim 14, wherein the patient subgroup score is generated pursuant to the following formula:

$$PSS(\%) = \frac{RSS_1 + RSS_2 + \ldots + RSS_n}{n}$$

wherein $RSS_i$ is the record strength score which is a total strength of completeness for an individual patient record constrained from 0 to 100% for an $i^{th}$ patient that meets the subpopulation condition; and n is a total number of patient records that meet the subpopulation condition.

16. The non-transitory computer-readable storage medium of claim 14, wherein the subpopulation condition is selected from a group consisting of age, race, gender, and insurance status.

17. The non-transitory computer-readable storage medium of claim 11, further comprising program code for generating a data field completeness score based on an average of binary completeness variables of a selected data field in a database;
wherein the data field completeness score indicates a percentage of all the selected data fields in the database that are complete;

wherein the data field completeness score is generated for all patients pursuant to the following formula:

$$DFCS_k(\%) = \frac{\sum_{1}^{n} X_{ik}}{n} \times 100$$

wherein $X_{ik}$ is a binary completeness variable for an $i^{th}$ patient wherein 1 represents a complete data field and 0 represents an incomplete data field; a $k^{th}$ data field, wherein k remains constant and i iterates for individual patients; and n is a total number of patient records.

18. The non-transitory computer-readable storage medium of claim 11, further comprising program code for comparing the strength of a selected data field for a subgroup across two or more databases using a data field completeness score based on an average of binary completeness variables of the selected data field in each database
wherein the data field completeness score indicates a percentage of all the selected data fields in each subgroup of each database that are complete;
wherein the data field completeness score is generated for the subgroup of patients pursuant to the following formula:

$$DFCS_k(\%) = \frac{\sum_{1}^{n} X_{ik}}{n} \times 100$$

wherein $X_{ik}$ is a binary completeness variable for an $i^{th}$ patient wherein 1 represents a complete data field and 0 represents an incomplete data field; a $k^{th}$ data field, wherein k remains constant and i iterates for individual patients that meet a subpopulation condition; and n is a total number of patient records that meet the subpopulation condition.

19. A method for managing health care patient record data from various independent healthcare facilities using independent healthcare software, the method comprising the steps of:
providing remote access to a plurality of databases over a network through a graphical user interface, wherein each database stores health care patient record data in a native format dependent on a software platform used at each healthcare facility;
accessing, by one or more processors, the plurality of databases containing native health care patient record data;
transforming native health care patient record data for a plurality of patients stored in the databases, using the one or more processors, to a standardized format based at least in part on concept mapping in which the native health care patient record data for each patient is converted into a plurality of parsed data fields;
assigning, by the one or more processors, a relative importance weight score to each of the plurality of data fields, wherein the relative importance weight score is a numerical value corresponding to the relative importance of each of the plurality of data fields;
generating, by the one or more processors, a numerical record strength score for the native health care patient record data for each patient, thereby converting the native health care patient record data for each patient from qualitative data to a numerical data set, the record strength determined based on the following formula:

$$RSS(\%) = \frac{(IW_1)(X_1) + (IW_2)(X_2) + (IW_3)(X_3) + \ldots + (IW_n)(X_n)}{\sum_{i=1}^{n} IW_i} \times 100$$

wherein RSS is the record strength score which is a total strength of completeness for the first patient's health care record constrained from 0 to 100%; $IW_i$ is the importance weight of $i^{th}$ data field; and $X_i$ is a binary completeness variable for $i^{th}$ data field wherein 1 represents a complete data field and 0 represents an incomplete data field; and
displaying on the graphic user interface the numerical record strength score of the native health care patient record data for each patient, thereby conveying a quantitative analysis of a completeness of the native health care patient record data for each patient.

20. The method of claim 1, wherein the user is a health care provider.

* * * * *